(12) United States Patent
Wu et al.

(10) Patent No.: US 11,160,271 B2
(45) Date of Patent: Nov. 2, 2021

(54) ANTI-FREEZING AGENT FOR PROTECTING BIOLOGICAL TISSUE DURING FREEZING TREATMENT AND PREPARATION METHOD THEREFOR

(71) Applicant: TAIPEI VETERANS GENERAL HOSPITAL, Taipei (TW)

(72) Inventors: Po Kuei Wu, Taipei (TW); Wei Ming Chen, Taipei (TW); Cheng Fong Chen, Taipei (TW); Jir You Wang, Taipei (TW); Wen Hai Wu, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 333 days.

(21) Appl. No.: 16/338,329

(22) PCT Filed: Sep. 30, 2016

(86) PCT No.: PCT/CN2016/101112
§ 371 (c)(1),
(2) Date: Mar. 29, 2019

(87) PCT Pub. No.: WO2018/058541
PCT Pub. Date: Apr. 5, 2018

(65) Prior Publication Data
US 2020/0022361 A1 Jan. 23, 2020

(51) Int. Cl.
*A01N 1/02* (2006.01)
(52) U.S. Cl.
CPC .................. *A01N 1/0221* (2013.01)

(58) Field of Classification Search
None
See application file for complete search history.

(56) References Cited

U.S. PATENT DOCUMENTS

2010/0008992 A1\* 1/2010 Ichim ..................... A61K 35/17
424/488
2011/0274666 A1 11/2011 Turner et al.

FOREIGN PATENT DOCUMENTS

| CN | 101342192 | \* | 1/2009 |
| CN | 101342192 | A | 1/2009 |
| CN | 102985130 | A | 3/2013 |
| CN | 103571439 | A | 2/2014 |

OTHER PUBLICATIONS

International Search Report issued in PCT/CN2016/101112 (PCT/ISA/210), dated Jul. 5, 2017.

\* cited by examiner

*Primary Examiner* — Ralph J Gitomer
(74) *Attorney, Agent, or Firm* — Birch, Stewart, Kolasch & Birch, LLP

(57) ABSTRACT

Disclosed are an anti-freezing agent for protecting a biological tissue from being damaged during a freezing treatment and a preparation method therefor. The method for preparing the anti-freezing agent involves mixing ethylene glycol, water and dimethylsulfoxide homogeneously to form a matrix, and then slowly adding sodium polyacrylate. The prepared anti-freezing agent is coated onto biological tissue during a freezing treatment such that damage to the biological tissue is reduced.

1 Claim, 3 Drawing Sheets

ANTI-FREEZING AGENT FOR PROTECTING BIOLOGICAL TISSUE DURING FREEZING TREATMENT AND PREPARATION METHOD THEREFOR

BACKGROUND OF THE INVENTION

Field of the Invention

The present invention relates to an anti-freezing agent and a method for preparing the same, and, in particular, to an anti-freezing agent used for protecting tissues during freezing treatment of human or animal tissues.

Description of the Prior Art

Malignant bone sarcoma, such as malignant osteosarcoma (Osteosarcoma), is a bone malignant tumor that often occurs in adolescents and children. During the surgery, we have to perform wide tumor resection and following limb reconstruction. The way of limb reconstruction includes tumor prosthesis and biological reconstruction. Compared to tumor prosthesis, biological reconstruction can achieve better longevity of limb function, so it is still more commonly used despite the difficulty and time consumption of surgery. Among them, frozen autograft uses "real bones" to reconstruct bone defect. However, the willingness to donate bones is not high, the source of allogeneic bone is limited, and the bone size and shape of each person are not the same, so there are still deficiencies in real use.

Although malignant bone sarcoma is a tumor that grows from inside or on the bone, in general, the bone that grows tumor does not necessarily have serious tumor destruction, even in osteoblastic osteosarcoma. Instead, more bones will grow out due to the tumor. For these patients, their bones are not completely destroyed, so these bones that are full of tumors but still have good texture can be taken out and subject to special treatment that kills the tumor cells to get a clean bone, just like resource recycling, which is called "recycled autograft". The biggest advantage of this method lies in that the bones are taken from the patient itself, so it is no need to worry about the size and shape of the bones as well as disease transmission. The so-called frozen autograft treated with liquid nitrogen means that the tumor-bearing bone is quickly immersed in liquid nitrogen at, for example, −196° C. for a period of time that ensure the tumor's central temperature to reach the lowest temperature, and then thawed slowly at room temperature. Tumor cells can be completely killed during such rapid freezing and slow thawing. In short, the principle of this cryopreservation is to reduce the temperature of the bone with tumor cells to a quite low temperature, so that water molecules inside and outside the bone cells undergo crystallization to form ice crystals, which can destroy the cell membrane and make the tumor cells die. However, during the freezing treatment, some surrounding innocent normal tissues, including cartilage, bone and tendon, will be destroyed at the same time. Therefore, how to protect the innocent normal tissues from being damaged by the freezing treatment is an issue that has yet to be solved.

SUMMARY OF THE INVENTION

The present invention is to provide a method of preventing the biological tissue from being damaged during the freezing treatment.

In one aspect, the present invention provides a method for preparing an anti-freezing agent, wherein the anti-freezing agent is used for protecting a biological tissue from being damaged during a freezing treatment for a biological tissue. The method comprises the following steps:

(1) mixing ethylene glycol and water to form an aqueous ethylene glycol solution, and then adding dimethyl sulfoxide into the aqueous ethylene glycol solution and mixing uniformly to form a matrix, wherein the weight ratio of ethylene glycol to water is about 1:1 to 3:1, and the weight ratio of dimethyl sulfoxide to the aqueous ethylene glycol solution is about 1:10 to 2:10; and (2) heating the matrix slowly and then adding sodium polyacrylate into the heated matrix, which is then stirred uniformly and cooled to room temperature to obtain the anti-freezing agent, wherein the weight ratio of the matrix to sodium polyacrylate is 4:1 to 10:1.

In one embodiment of the invention, the water is physiological saline.

In one embodiment of the invention, sodium polyacrylate is sodium polyacrylate having a molecular weight of 120,000.

In one embodiment of the invention, the weight ratio of ethylene glycol to water is about 2:1.

In one embodiment of the invention, the weight ratio of dimethyl sulfoxide to the aqueous ethylene glycol solution is about 1:10.

In one embodiment of the invention, the weight ratio of the matrix to sodium polyacrylate is about 10:1.

In one embodiment of the invention, the matrix prepared in step (3) is slowly heated and kept at about 70° C.

According to an embodiment of the present invention, the method for preparing an anti-freezing agent of the present invention comprises the following steps:

(1) mixing ethylene glycol and water to form the aqueous ethylene glycol solution, and then adding dimethyl sulfoxide into the aqueous ethylene glycol solution and mixing uniformly to form the matrix, wherein the weight ratio of ethylene glycol to water is about 2:1, and the weight ratio of dimethyl sulfoxide to the aqueous ethylene glycol solution is about 1:10; and (2) heating the matrix slowly and keeping at about 70° C., and then adding sodium polyacrylate slowly into the heated matrix, which is then stirred uniformly and cooled to room temperature to obtain the anti-freezing agent, wherein the weight ratio of the matrix to sodium polyacrylate is about 10:1.

Another aspect of the present invention provides an anti-freezing agent, which is prepared by the method of the present invention described above.

A further aspect of the present invention provides a method for protecting a biological tissue of a human or animal during a freezing treatment, comprising applying the anti-freezing agent prepared by the method described above to the biological tissue to protect the biological tissue from being damaged during the freezing treatment.

In one embodiment of the present invention, the biological tissue of the human or animal is cartilage, tendon or ligament. In a particular embodiment of the present invention, it is used to prepare a recycled bone autograft.

A further aspect of the present invention provides a recycled bone autograft obtained by taking an autologous bone with tumor cells from a patient with bone tumor, killing the tumor cells of the autologous bone by a freezing treatment, and protecting the cartilage, tendon or ligament of the autologous bone with the anti-freezing agent of the present invention.

In one embodiment of the present invention, the bone osteoma is malignant bone osteoma.

The recycled bone autograft prepared by the method of the present invention can avoid worry about bone size and shape difference and will not cause disease infection because the bone is taken from the patient itself. In addition, the normal biological tissues will not be destroyed simultaneously when the tumor cells are killed by the freezing treatment due to the protection of the anti-freezing agent of the present invention.

DETAILED DESCRIPTION OF THE EMBODIMENTS

Example 1

Preparation of the Anti-Freezing Agent of the Present Invention

Figure 1:
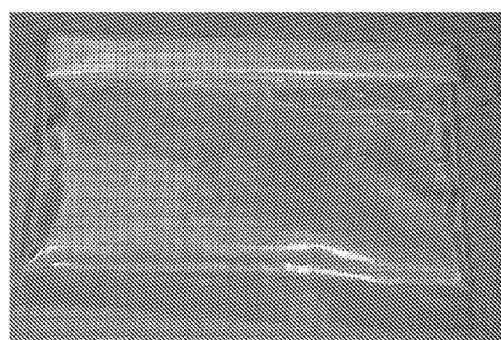
FIG. 1 shows an anti-freezing agent made in accordance with the present invention and having a transparent and viscous appearance.

At room temperature, 63 g of ethylene glycol, 27 g of physiological saline, and 10 g of dimethyl sulfoxide (DMSO) were mixed and stirred uniformly to prepare an antifreeze matrix. Afterwards, 30-70 g of the antifreeze matrix was heated to and kept at 70° C. in a water bath, and then 5-7 g of sodium polyacrylate (MW: 120,000) was slowly added into the antifreeze matrix, followed by cooling to room temperature with uniform stirring, thereby obtaining the anti-freezing agent of the present invention. The appearance of the anti-freezing agent is transparent and viscous, as shown in FIG. 1.

Example 2

Figure 2:
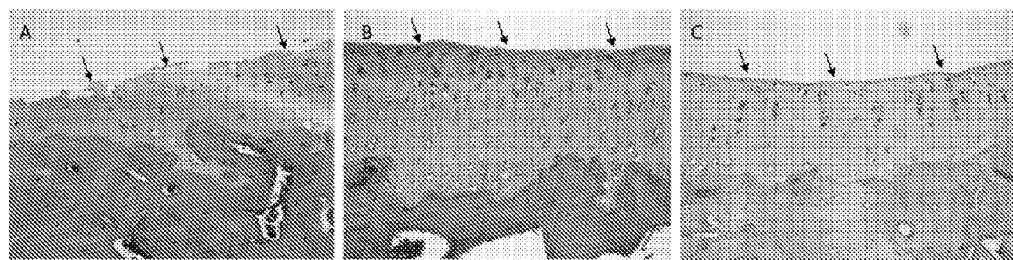
FIG. 2 shows the protective effect of the anti-freezing agent of the present invention on rat bone tissues. Compared with the control groups, the anti-freezing agent of the present invention can protect cartilage tissues and avoid fragmentation caused by the freezing treatment.

Protective Effect of the Anti-Freezing Agent of the Present Invention on Rat Bone Tissues The rat knee cartilage was taken out. The control group A was not treated, and the control group B was coated with a conventional commercially available anti-freezing agent (dimethyl sulfoxide) at the articular cartilage. The experimental groups were coated with the anti-freezing agent of the present invention at the articular cartilage, separately placed in liquid nitrogen for 20 minutes, slowly warmed to room temperature for 20 minutes, fixed with 4% paraformaldehyde, pathologically sectioned, and then stained with hematoxylin-eosin (HE stain). The pathological sections of hematoxylin-eosin stained control group (A), control group (B), and experimental group (C). are shown in FIG. 2. After freezing, in the control group A the cartilage surface became brittle and uneven (as indicated by the arrow), and the control group B was also uneven (as indicated by the arrow). However, in the experimental group C, the intact cartilage surface was visible (as indicated by the arrow), showing that the anti-freezing agent of the present invention protects the cartilage tissue from fragmentation caused by the antifreeze treatment.

Example 3

Figure 3:
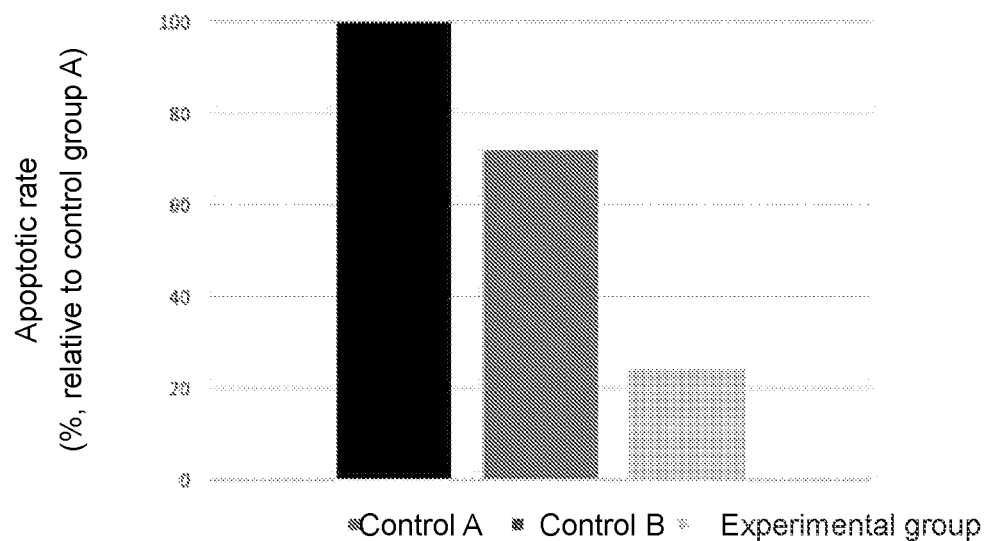
FIG. 3 shows the effect of the anti-freezing agent of the present invention on apoptosis of rat chondrocytes. Compared with the control groups, the anti-freezing agent of the present invention can reduce apoptosis caused by the freezing treatment.

Effect of the Anti-Freezing Agent of the Present Invention on Apoptosis of Rat Chondrocytes The control group A, control group B, and experimental group C described above were subjected to apoptosis analysis (TUNEL assay) to verify whether the anti-freezing agent of the present invention can avoid the deoxyribonucleic acid (DNA) of the chondrocytes from fragmentation caused by freezing. The experimental results are shown in FIG. 3. It can be found that the proportion of TUNEL-positive cells (representing apoptosis of the tumor cells) in the experimental group C is significantly lower than that of the control group A and the control group B, indicating that the anti-freezing agent of the present invention can reduce apoptosis.

Example 4

Figure 4:
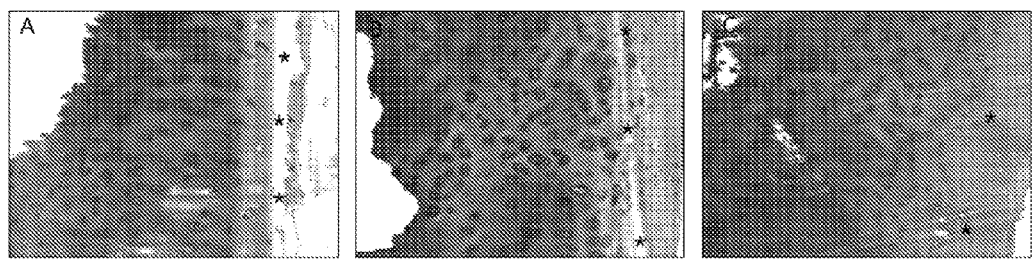
FIG. 4 shows the protective effect of the anti-freezing agent of the present invention on human tissues. Compared with the control groups, the anti-freezing agent of the present invention can reduce the separation of cartilage from hard bone caused by freezing.

Protection Effect of the Anti-Freezing Agent of the Present Invention on Human Cartilage Tissue Unneeded normal cartilage tissues (residual specimens) taken from the human body during surgery were divided into three groups and treated separately: control group A was not treated; for control group B, traditional commercially available anti-freezing agent was applied to articular cartilage; and for experimental group C, the anti-freezing agent of the present invention was applied to the articular cartilage. The control and experimental groups were separately placed in liquid nitrogen to freeze for 20 minutes, slowly warmed to room temperature for 20 minutes, fixed with 4% paraformaldehyde, pathologically sectioned, and then stained by hematoxylin-eosin. The results are shown in FIG. 4. After freezing, separation occurred at the intersection (the stellate) of the cartilage bottom and the hard bone in the control group A, separation (the stellate) also occurred in the control group B, but in the experimental group C it can be seen that the contact surface between the cartilage bottom and the hard bone is normally joined together. The size of separation was 2.16 mm in the control group A, 1.2 mm in the control group B, and 0.45 mm in the experimental group. It was shown that the anti-freezing agent of the present invention can protect cartilage tissue and reduce the separation of cartilage and hard bone caused by freezing.

Example 5

Figure 5:
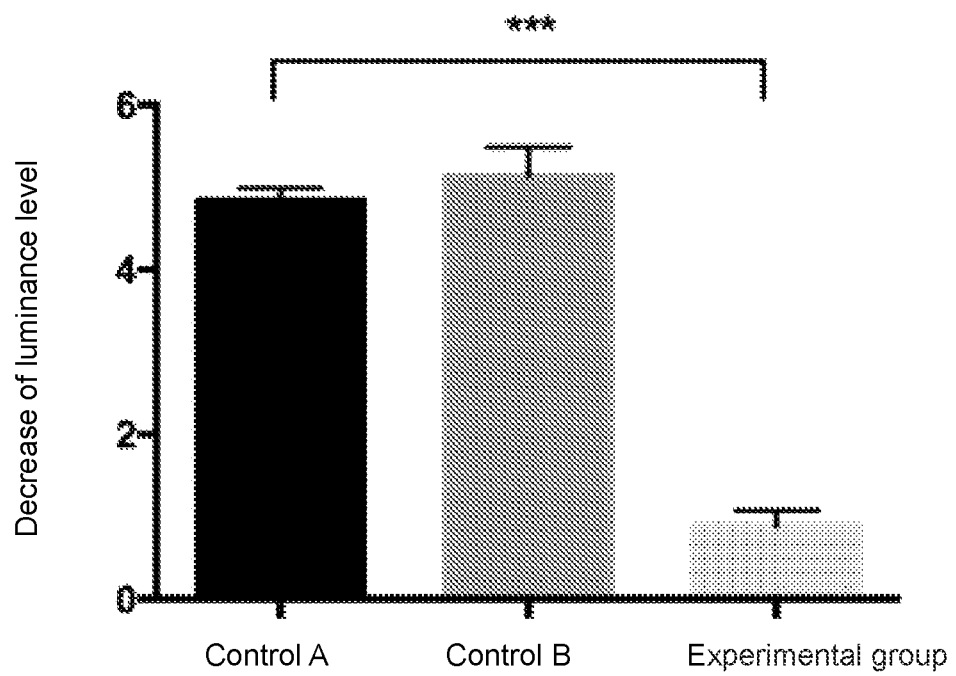
FIG. 5 shows the effect of the anti-freezing agent of the present invention on the change of cartilage color index after freezing. Compared with the control groups, the anti-freezing agent of the present invention can alleviate the change of cartilage color index caused by freezing.

Effect of the Anti-Freezing Agent of the Present Invention on the Change of Cartilage Color Index After Freezing Unneeded normal cartilage tissues (residual specimens) taken from the human body during surgery were divided into three groups and treated separately: control group A was not treated; for control group B, traditional commercially available anti-freezing agent was applied to articular cartilage; and for experimental group C, the anti-freezing agent of the present invention was applied to the articular cartilage. The control and experimental groups were separately placed in liquid nitrogen to freeze for 20 minutes, and then slowly warmed to room temperature for 20 minutes. The color index change of the cartilage surface was observed by analyzing the decrease of luminance level of the cartilage surface. The results are shown in FIG. 5. For the control group A and the control group B, after freezing, the luminance level of the cartilage surface was significantly decreased, indicating that the moisture in the cartilage tissue was largely released after freezing. However, the decrease in the experimental group C was rather small, indicating that the anti-freezing agent of the present invention can alleviate the change of cartilage color index caused by freezing, and the moisture in the cartilage tissues did not largely escape after freezing.

In summary, the anti-freezing agent of the present invention can protect the biological tissue from damage caused by freezing during the freezing treatment. Obviously, the anti-freezing agent of the present invention can be used for biological tissue protection during the freezing treatment.

What is claimed is:

1. An anti-freezing agent, wherein the anti-freezing agent is prepared by the following steps:
   (1) mixing ethylene glycol and water to form an aqueous ethylene glycol solution, and then adding dimethyl sulfoxide into the aqueous ethylene glycol solution and mixing uniformly to form a matrix, wherein a weight ratio of ethylene glycol to water is about 1:1 to 3:1, and a weight ratio of dimethyl sulfoxide to the aqueous ethylene glycol solution is about 1:10 to 2:10; and
   (2) heating the matrix slowly and then adding sodium polyacrylate into the heated matrix, which is then stirred uniformly and cooled to room temperature to obtain the anti-freezing agent, wherein a weight ratio of the matrix to sodium polyacrylate is 4:1 to 10:1.

* * * * *